United States Patent
Brown et al.

(10) Patent No.: US 10,319,575 B2
(45) Date of Patent: Jun. 11, 2019

(54) METHOD OF INTRODUCING IONS INTO A VACUUM REGION OF A MASS SPECTROMETER

(71) Applicant: Micromass UK Limited, Wilmslow (GB)

(72) Inventors: Jeffery Mark Brown, Hyde (GB); Martin Raymond Green, Bowdon (GB)

(73) Assignee: MICROMASS UK LIMITED, Wilmslow (GB)

( * ) Notice: Subject to any disclaimer, the term of this patent is extended or adjusted under 35 U.S.C. 154(b) by 0 days.

(21) Appl. No.: 15/501,599

(22) PCT Filed: Aug. 5, 2015

(86) PCT No.: PCT/GB2015/052264
§ 371 (c)(1),
(2) Date: Feb. 3, 2017

(87) PCT Pub. No.: WO2016/020678
PCT Pub. Date: Feb. 11, 2016

(65) Prior Publication Data
US 2017/0221690 A1 Aug. 3, 2017

(30) Foreign Application Priority Data
Aug. 5, 2014 (EP) .................................... 14179810
Aug. 5, 2014 (GB) ................................... 1413817.6

(51) Int. Cl.
H01J 49/04 (2006.01)
G01N 27/62 (2006.01)
H01J 49/00 (2006.01)

(52) U.S. Cl.
CPC ........ *H01J 49/0495* (2013.01); *G01N 27/622* (2013.01); *H01J 49/0031* (2013.01); *H01J 49/0409* (2013.01); *H01J 49/0418* (2013.01)

(58) Field of Classification Search
None
See application file for complete search history.

(56) References Cited

U.S. PATENT DOCUMENTS 3,534,945 A 10/1970 Sweeney
6,871,556 B2 3/2005 Andresen et al.
(Continued)

FOREIGN PATENT DOCUMENTS

DE 19820626 11/1999
FR 2895513 6/2007

OTHER PUBLICATIONS

Vas et al., Solid-phase microextraction: a powerful sample preparation tool prior to mass spectrometric analysis, 39 J. Mass Spectrom. 233 (2004).*

(Continued)

*Primary Examiner* — James Choi
(74) *Attorney, Agent, or Firm* — Womble Bond Dickinson (US) LLP; Deborah M. Vernon; Heath T. Misley

(57) ABSTRACT

A method of mass or ion mobility spectrometry is disclosed. The method comprises providing a spectrometer comprising an orifice between an atmospheric and a sub-atmospheric pressure region of the spectrometer, wherein the latter comprises an ion guide or ion trap; providing a sample probe comprising a needle assembly on which a sample is deposited or that is supplied with a sample; inserting the needle assembly through the orifice into the sub-atmospheric pressure region so that the sample is arranged within or adjacent to the ion guide or trap in the sub-atmospheric pressure region; and then desorbing the sample from the needle assembly within the sub-atmospheric pressure region and/or (Continued)

ionizing the sample within the sub-atmospheric pressure region so as to generate ions that enter the ion guide or ion trap. The proximity of the sample to the ion guide or trap allows analyte ions from the sample to be captured efficiently.

11 Claims, 4 Drawing Sheets

(56) References Cited

U.S. PATENT DOCUMENTS

| | | | |
|---|---|---|---|
| 7,119,342 | B2 | 10/2006 | Syage et al. |
| 7,405,397 | B2 | 7/2008 | Covey et al. |
| 7,671,344 | B2 | 3/2010 | Tang et al. |
| 7,893,401 | B2 | 2/2011 | Ding |
| 8,063,362 | B1 | 11/2011 | Dressler et al. |
| 8,368,013 | B2 | 2/2013 | Ishimaru et al. |
| 8,704,170 | B2 | 4/2014 | Kumashiro et al. |
| 8,956,445 | B2 | 2/2015 | Armstrong et al. |
| 9,105,458 | B2 | 8/2015 | Trimpin et al. |
| 9,184,037 | B2 | 11/2015 | Kumano et al. |
| 2002/0175278 | A1* | 11/2002 | Whitehouse ........ H01J 49/0095 250/281 |
| 2005/0287679 | A1* | 12/2005 | Pawliszyn ............. A61B 5/417 436/174 |
| 2009/0057551 | A1* | 3/2009 | Tang ..................... H01J 49/066 250/288 |
| 2011/0253889 | A1* | 10/2011 | Ishimaru ............... H01J 49/145 250/282 |
| 2014/0030818 | A1 | 1/2014 | Schueler et al. |

OTHER PUBLICATIONS

Yan Wang, "*Laser Desorption Solid Phase Microextraction*", http://citeseerx.ist.psu.edu/viewdoc/downioad?doi=10.1.1.65.432&rep=rep1&type=pdf, Jan. 1, 2006.

Hui Tong et al., "*Solid Phase Microextraction with Matrix Assisted Laser Desorption/Ionization Introduction to Mass Spectrometry and Ion Mobility Spectrometry Presented at Pittcon 2002*", The Analyst, vol. 127, No. 9, pp. 1207-1210, (Aug. 2002).

György Vas et al., "*Solid-phase Microextraction: a Powerful Sample Preparation Tool Prior to Mass Spectrometric Analysis*", Journal of Mass Spectrometry, vol. 39, No. 3, pp. 233-254, (Mar. 2004).

* cited by examiner

METHOD OF INTRODUCING IONS INTO A VACUUM REGION OF A MASS SPECTROMETER

CROSS-REFERENCE TO RELATED APPLICATIONS

This application represents the U.S. National Phase of International Application number PCT/GB2015/052264 entitled "Method of Introducing Ions into a Vacuum Region of a Mass Spectrometer" filed 5 Aug. 2015, which claims priority from and the benefit of United Kingdom patent application No. 1413817.6 filed on 5 Aug. 2014 and European patent application No. 14179810.8 filed on 5 Aug. 2014. The entire contents of these applications are incorporated herein by reference.

BACKGROUND TO THE PRESENT INVENTION

The present invention relates to a method of introducing a sample into a mass spectrometer or ion mobility spectrometer.

Low volatility analytes may be ionised from solution or by desorption at atmospheric pressure by techniques such as Electrospray ionisation (ESI), Atmospheric Pressure Chemical Ionisation (APCI), Atmospheric Pressure Matrix Assisted Laser Desorption Ionisation (AP-MALDI), Atmospheric Solids Analysis Probe (ASAP), Desorption Electrospray Ionisation (DESI) and Direct Analysis in Real Time (DART) etc. In order to mass analyse the resulting analyte ions, the ions must be introduced ions into a sub-ambient region of a mass spectrometer. An orifice is provided between the atmospheric pressure region in which the ions are ionised and the low pressure region of the mass spectrometer. In general, the larger the orifice is the more ions are passed into the mass spectrometer, for a given concentration of analyte. However, the larger the orifice is the greater the gas flow into the mass spectrometer. This is undesirable because expensive vacuum pumping equipment must be used in order to maintain the desired pressure within the mass spectrometer, particularly in the region of the analyser.

In contrast, sub-atmospheric pressure ionisation sources can be interfaced with the mass spectrometer without requiring pumping of such high gas loads from the vacuum chamber of the mass spectrometer. Examples of sub-atmospheric pressure ionisation sources include glow discharge, MALDI, electron impact, chemical ionisation and Matrix assisted inlet ionization ion sources. Introduction of low volatility sample material into these sources is typically achieved via a vacuum lock in which a sample stage is introduced into a separate chamber and this chamber partially evacuated before allowing the vacuum chamber of the mass spectrometer to be in fluid contact with this separate chamber. This avoids a large volume of gas entering the mass spectrometer. However, these vacuum locks are mechanically cumbersome, expensive and require additional rough pumping.

It is desired to provide an improved method of mass spectrometry or ion mobility spectrometry and an improved spectrometer.

SUMMARY OF THE PRESENT INVENTION

From a first aspect the present invention provides a method of mass spectrometry or ion mobility spectrometry comprising:

providing a spectrometer comprising an orifice between an atmospheric pressure region and a sub-atmospheric pressure region of the spectrometer, wherein the sub-atmospheric pressure region comprises an ion guide or ion trap;

providing a sample probe comprising a needle assembly on which a sample is deposited or that is supplied with a sample;

inserting the needle assembly through the orifice and into the sub-atmospheric pressure region so that the sample is arranged within or adjacent to the ion guide or ion trap in the sub-atmospheric pressure region; and then desorbing the sample from the needle assembly within the sub-atmospheric pressure region and/or ionising the sample within the sub-atmospheric pressure region so as to generate ions that enter the ion guide or ion trap.

The present invention provides a simple and effective method of introducing a sample into a vacuum region of a spectrometer with minimal introduction of air or other gas and therefore with minimal gas load on any pumping system in the spectrometer. The present invention therefore enables a sample to be introduced anywhere in the spectrometer without having to add extra pumping or vacuum locks. As the needle assembly is inserted so that the sample is arranged within or adjacent to the ion guide or ion trap, analyte ions from the sample are captured efficiently.

US 2011/0253889 discloses inserting a solid phase microextraction (SPME) fibre into an ionisation chamber of a mass spectrometer in order to insert a sample into the ionisation chamber. A plasma is then generated so as to ionise the sample on the SPME fibre. However, this document does not disclose or suggest inserting the fibre into the ionisation chamber so that the sample is arranged within or adjacent to an ion guide or ion trap. As such, the instrument is less able to efficiently capture analyte ions from the sample. It would not be obvious to modify the technique of US'889 so as to arrange the SPME fibre in or adjacent to an ion guide or ion trap as the SPME fibre must be exposed to the plasma.

The sub-atmospheric pressure region may be maintained at a pressure selected from the group consisting of: <1000 mbar; ≤500 mbar; ≤1 mbar; ≤5×10$^{-1}$ mbar; ≤10$^{-1}$ mbar; ≤5×10$^{-2}$ mbar; ≤10$^{31\ 2}$ mbar; ≤5×10$^{-3}$ mbar; ≤10$^{-3}$ mbar; ≤5×10$^{-4}$ mbar; ≤10$^{-4}$ mbar; ≤5×10$^{-5}$ mbar; and ≤5×10$^{-5}$ mbar.

The sample comprises analyte to be ionised so as to form analyte ions within the spectrometer. The sample may or may not comprise an additional matrix. Alternatively, or additionally, the sample may comprise reagent to be ionised to form reagent ions in the spectrometer.

The sample may be deposited directly onto the part of the needle assembly that enters the sub-atmospheric pressure region.

The sub-atmospheric pressure region may be an ionisation region of the mass spectrometer.

The spectrometer may comprise a septum, film or membrane arranged over the orifice that initially forms a gas seal between the atmospheric pressure region and the sub-atmospheric pressure region, and wherein the step of inserting the needle assembly through the orifice comprises piercing the septum, film or membrane with a needle of the needle assembly.

It will be appreciated that the orifice is an aperture through the material forming the substantive wall of the sub-atmospheric pressure region, which may or may not be covered by the septum, film or membrane.

The septum, film or membrane is formed from a solid material.

The septum, film or membrane may be configured such that when the needle is withdrawn from the septum, film or membrane the septum, film or membrane substantially maintains said gas seal so as to substantially prevent leakage of gas from the atmospheric pressure region into the sub-atmospheric pressure region. For example, the septum may be a silica rubber septum.

The sample may be deposited on the needle assembly is a sample in the solid phase.

The sample is in the solid phase at least at atmospheric temperature and pressure.

The needle assembly described herein may comprise a hollow needle, and the sample may be deposited on the inside surface of the hollow needle.

The needle assembly may comprise a hollow needle and a substrate member on which the sample is located, absorbed or adsorbed; wherein the substrate is housed within the hollow needle.

The substrate member may be an SPME device and/or a fused silica fibre.

The SPME device or substrate member may comprise a coating of liquid polymer material and/or solid sorbent material for absorbing or adsorbing said sample.

The method may comprise loading the sample onto the needle assembly by absorbing or adsorbing one or more analyte or other chemical (e.g. reagent) from a sample solution onto the SPME device, substrate member, fibre or coating.

The sample can be extracted or pre-concentrated using existing methods of solid phase extraction and then introduced directly into the spectrometer.

Alternatively, the substrate member may be metal or glass.

The needle assembly may comprise a solid phase microextraction (SPME) device for holding the sample.

The needle assembly may comprise a hollow needle and a substrate member on which the sample is located, absorbed or adsorbed; wherein the substrate member is extendable from within the hollow needle. The step of inserting the needle assembly through the orifice may comprise inserting said hollow needle through the orifice, septum, film or membrane whilst the substrate member is retracted inside the hollow needle; wherein when the hollow needle is inside the sub-atmospheric pressure region the substrate member is extended out from within the hollow needle; and wherein the sample on the extended substrate member is then desorbed and/or ionised.

The substrate member may also be retractable into the hollow needle, e.g. prior to extraction of the needle through the orifice, or to locate the sample in the correct position within the sub-atmospheric pressure chamber.

The probe assembly may comprise a syringe plunger connected to the substrate member, and the plunger may be used for extending and retracting the substrate member out of and into the hollow needle.

The method may comprise evaporating solvent in the sample before inserting the needle assembly into the spectrometer.

The ion guide or ion trap may be formed from electrodes and voltages may be applied to said electrodes so as to confine sample ions generated from said sample in one, two or three dimensions within said ion guide or ion trap.

The ion guide or ion trap may be an RF ion guide or ion trap. The method comprises ionising the sample so as to form ions within the ion guide or ion trap, and RF voltages may be applied to said ion guide or ion trap so as to confine the ions in one, two or three dimensions within the ion guide or ion trap.

The ion guide or ion trap may be an extended ion guide or ion trap having a longitudinal axis. The needle assembly may be inserted into the ion guide or ion trap along the axis of the ion guide or ion trap or through gaps between electrodes forming the ion guide or ion trap.

Ions confined in the ion guide or ion trap may be driven along the ion guide or ion trap and/or towards the exit of the ion guide or ion trap by successively applying a voltage pulse (e.g. one or more DC voltages) to successive electrodes forming the ion guide or ion trap. Alternatively, or additionally, a DC voltage gradient may be arranged along the ion guide or ion trap so as to drive ions along the ion guide or ion trap and/or towards the exit of the ion guide or ion trap.

The ion guide or ion trap may form part of a fragmentation cell that fragments the sample ions, a reaction cell that reacts the sample ions with other ions or molecules, a mass analyser that analyses the sample ions, or an ion mobility analyser that analyses the sample ions.

The step of inserting the needle assembly into the sub-atmospheric pressure region so that the sample is adjacent to the ion guide or ion trap may comprise arranging the sample to be within a distance x mm of the ion guide or ion trap, wherein x is selected from the group consisting of: $\leq 10$; $\leq 9$; $\leq 8$; $\leq 7$; $\leq 6$; $\leq 5$; $\leq 4$; $\leq 3$; $\leq 2$; and $\leq 1$.

The sample may be ionised within the sub-atmospheric pressure region by directing a laser or other light source onto the sample; and/or by Matrix Assisted Ionization in Vacuum (MAIV); and/or by Matrix Assisted Laser Desorption Ionization (MALDI).

Alternatively, or additionally, the sample may be ionised within the sub-atmospheric pressure region by one or more of the following techniques: glow discharge ionisation; Electron impact ionisation; Chemical ionization; Fast Atom Bombardment (FAB); Liquid Secondary Ion Mass Spectrometry (LSIMS); metastable atom bombardment (MAB); or bombardment with ions, electrons or excited neutrals at sub-ambient pressure.

The method may comprise heating the needle assembly, needle or substrate member. The heating may desorb and/or ionise the sample or may assist in desorbing and/or ionising the sample. The heating may be performed by resistive heating, conduction or infra-red radiation.

The method may comprise applying a DC and/or AC voltage to said needle assembly, needle or substrate member. The application of the voltage(s) may desorb and/or ionise the sample or may assist in desorbing and/or ionising the sample.

The needle assembly may form at least a part of an electrospray ionisation ion source, and said method may comprise supplying a sample solution to the needle assembly whilst the needle assembly is located in the sub-atmospheric pressure region and electrospraying the sample from the needle assembly.

The orifice may have substantially the same cross-sectional size and shape as the portion of the needle assembly that is injected through the orifice.

The spectrometer may be a portable spectrometer such as a small field portable mass spectrometer or ion mobility spectrometer. This may be used, for example, for direct sampling from complex matrices such as milk, blood or saliva etc.

The method of mass spectrometry or ion mobility spectrometry further comprises mass analysing or ion mobility analysing ions which have been generated from the sample.

Methods are also contemplated wherein the sample is not arranged within or adjacent to the ion guide. Accordingly, from a second aspect the present invention provides a method of introducing a sample into a sub-atmospheric pressure region of a mass spectrometer or ion mobility spectrometer, said method comprising:

providing an orifice between an atmospheric pressure region and said sub-atmospheric pressure region of said spectrometer;

providing a sample probe comprising a needle assembly on which a sample is deposited or that is supplied with a sample;

inserting the needle assembly through the orifice and into the sub-atmospheric pressure region so that the sample is arranged in the sub-atmospheric pressure region; and then desorbing the sample from the needle assembly within the sub-atmospheric pressure region and/or ionising the sample within the sub-atmospheric pressure region.

This method may comprise any of the optional features described herein, such as those described in relation to the first aspect of the present invention, and need not necessarily include the features of arranging the sample in or adjacent to an ion guide or ion trap.

From a third aspect the present invention provides a method of mass spectrometry or ion mobility spectrometry comprising:

providing a spectrometer having an atmospheric pressure region, a sub-atmospheric pressure region comprising an ion guide or ion trap, and an orifice between the atmospheric pressure region and sub-atmospheric pressure region;

providing a sample probe comprising a needle assembly having a solid phase micro-extraction (SPME) device holding a sample in solid phase;

inserting the needle assembly through the orifice and into the sub-atmospheric pressure region so that the sample is arranged within or adjacent to the ion guide or ion trap in the sub-atmospheric pressure region; and then directing a laser onto the sample to ionise the sample within the sub-atmospheric pressure region so as to generate ions that enter the ion guide or ion trap.

This method may comprise any of the optional features described herein, such as those described in relation to the first aspect of the present invention.

The present invention also provides a mass spectrometer or ion mobility spectrometer comprising:

a vacuum chamber comprising an ion guide or ion trap, a vacuum pump for maintaining the vacuum chamber at sub-atmospheric pressure, and an orifice in the wall of the vacuum chamber for receiving a needle assembly from outside of the spectrometer for delivering a sample into the vacuum chamber;

wherein the ion guide or ion trap is arranged proximate the orifice so that when the needle assembly is inserted through the orifice the sample is arranged within or adjacent to the ion guide or ion trap; and wherein the spectrometer comprises a desorption or ionising mechanism for desorbing the sample from the needle assembly within the vacuum chamber and/or for ionising the sample within the vacuum chamber.

The region outside of the spectrometer is at atmospheric pressure.

The ion guide or ion trap may be arranged within a distance y mm of the orifice so that when the needle assembly is inserted through the orifice the sample is arranged within or adjacent to the ion guide or ion trap; wherein y is selected from the group consisting of: $\leq 40$; $\leq 35 \leq 30$; $\leq 25$; $\leq 20$; $\leq 15$; $\leq 10$; $\leq 9$; $\leq 8$; $\leq 7$; $\leq 6$; $\leq 5$; $\leq 4$; $\leq 3$; $\leq 2$; and $\leq 1$.

The spectrometer may be configured to perform any of the methods described herein.

For example, the vacuum pump may be configured so as to maintain the vacuum chamber at a pressure selected from the group consisting of: $<1000$ mbar; $\leq 500$ mbar; $\leq 1$ mbar; $\leq 5\times 10^{-1}$ mbar; $\leq 10^{-1}$ mbar; $\leq 5\times 10^{-2}$ mbar; $\leq 10^{-2}$ mbar; $\leq 5\times 10^{-3}$ mbar; $\leq 10^{-3}$ mbar; $\leq 5\times 10^{-4}$ mbar; $\leq 10^{-4}$ mbar; $\leq 5\times 10^{-5}$ mbar; and $\leq 5\times 10^{-5}$ mbar.

The vacuum chamber may be an ionisation region of the mass spectrometer.

The spectrometer may further comprise a septum, film or membrane arranged over the orifice that forms a gas seal between the vacuum chamber and the outside of the spectrometer.

It will be appreciated that the orifice is an aperture through the material forming the substantive wall of the vacuum chamber, which may or may not be covered by the septum, film or membrane.

The septum, film or membrane is formed from a solid material.

The septum, film or membrane may be configured such that when the needle is withdrawn from the septum, film or membrane the septum, film or membrane substantially maintains said gas seal so as to substantially prevent leakage of gas from the atmospheric pressure region into the sub-atmospheric pressure region. For example, the septum may be a silica rubber septum.

The ion guide or ion trap may be formed from electrodes and voltages may be applied to said electrodes so as to confine sample ions generated from said sample in one, two or three dimensions within said ion guide or ion trap.

The ion guide or ion trap may be an RF ion guide or ion trap. The spectrometer may be configured to apply RF voltages to said ion guide or ion trap so as to confine the ions in one, two or three dimensions within the ion guide or ion trap.

The ion guide or ion trap may be an extended ion guide or ion trap having a longitudinal axis, and may be arranged and configured so that the needle assembly may be inserted through the orifice (e.g. inserted coaxially with the orifice) into the ion guide or ion trap along the axis of the ion guide or ion trap; or through gaps between electrodes forming the ion guide or ion trap.

The spectrometer may be configured to confine ions in the ion guide or ion trap and drive the ions along the ion guide or ion trap and/or towards the exit of the ion guide or ion trap by successively applying a voltage pulse (e.g. one or more DC voltages) to successive electrodes forming the ion guide or ion trap. Alternatively, or additionally, the spectrometer may be configured to arrange a DC voltage gradient along the ion guide or ion trap so as to drive ions along the ion guide or ion trap and/or towards the exit of the ion guide or ion trap.

The ion guide or ion trap may form part of a fragmentation cell for fragmenting the sample ions, a reaction cell for reacting the sample ions with other ions or molecules, a mass analyser for mass analysing the sample ions, or an ion mobility analyser for analysing the sample ions.

The spectrometer may comprise a laser or other light source arranged and configured for ionising the sample.

Alternatively, or additionally, the spectrometer may comprise other means for ionising the sample. For example, the sample may be ionised within the vacuum chamber by one or more of the following techniques: glow discharge ionisation; Electron impact ionisation; Chemical ionization; Fast Atom Bombardment (FAB); Liquid Secondary Ion Mass Spectrometry (LSIMS); metastable atom bombardment (MAB); or bombardment with ions, electrons or excited neutrals at sub-ambient pressure.

The spectrometer may comprise a heater for heating the needle assembly or needle. The heating may desorb and/or ionise the sample or may assist in desorbing and/or ionising the sample. The heating may be performed by resistive heating, conduction or infra-red radiation.

The spectrometer may comprise a voltage supply for applying a DC and/or AC voltage to said needle assembly or needle. The application of the voltage(s) may desorb and/or ionise the sample or may assist in desorbing and/or ionising the sample.

The needle assembly may form at least a part of an electrospray ionisation ion source.

The orifice may have substantially the same cross-sectional size and shape as the portion of the needle assembly that is injected through the orifice.

The spectrometer may be a portable spectrometer such as a small field portable mass spectrometer or ion mobility spectrometer.

The spectrometer further comprises a mass analyser or ion mobility analyser for analysing ions which have been generated from the sample.

The present invention also provides a kit of a sample probe and a mass spectrometer or ion mobility spectrometer that are configured to perform any one of the methods described herein.

Accordingly, the present invention provides a kit comprising a mass spectrometer or an ion mobility spectrometer and a sample probe having a needle assembly for delivering a sample into the spectrometer;

wherein said spectrometer comprises a vacuum chamber, a vacuum pump for maintaining the vacuum chamber at sub-atmospheric pressure, and an orifice in the wall of the vacuum chamber for fluidly connecting said vacuum chamber to the outside of the spectrometer and for receiving a sample from outside the spectrometer;

wherein the sample probe comprises a needle assembly configured to be inserted through the orifice from the outside of the spectrometer into the vacuum chamber for delivering the sample into the vacuum chamber; and wherein the spectrometer comprises means for desorbing the sample from the needle assembly within the vacuum chamber and/or means for ionising the sample within the vacuum chamber.

The sample probe and/or spectrometer may be arranged or configured as described herein above, or for performing the methods described herein. For example, the sample probe and/or spectrometer may have features described above in relation to the various aspects of the present invention.

The spectrometer may comprise:

(a) an ion source selected from the group consisting of: (i) an Electrospray ionisation ("ESI") ion source; (ii) an Atmospheric Pressure Photo Ionisation ("APPI") ion source; (iii) an Atmospheric Pressure Chemical Ionisation ("APCI") ion source; (iv) a Matrix Assisted Laser Desorption Ionisation ("MALDI") ion source; (v) a Laser Desorption Ionisation ("LDI") ion source; (vi) an Atmospheric Pressure Ionisation ("API") ion source; (vii) a Desorption Ionisation on Silicon ("DIOS") ion source; (viii) an Electron Impact ("EI") ion source; (ix) a Chemical Ionisation ("CI") ion source; (x) a Field Ionisation ("FI") ion source; (xi) a Field Desorption ("FD") ion source; (xii) an Inductively Coupled Plasma ("ICP") ion source; (xiii) a Fast Atom Bombardment ("FAB") ion source; (xiv) a Liquid Secondary Ion Mass Spectrometry ("LSIMS") ion source; (xv) a Desorption Electrospray Ionisation ("DESI") ion source; (xvi) a Nickel-63 radioactive ion source; (xvii) an Atmospheric Pressure Matrix Assisted Laser Desorption Ionisation ion source; (xviii) a Thermospray ion source; (xix) an Atmospheric Sampling Glow Discharge Ionisation ("ASGDI") ion source; (xx) a Glow Discharge ("GD") ion source; (xxi) an Impactor ion source; (xxii) a Direct Analysis in Real Time ("DART") ion source; (xxiii) a Laserspray Ionisation ("LSI") ion source; (xxiv) a Sonicspray Ionisation ("SSI") ion source; (xxv) a Matrix Assisted Inlet Ionisation ("MAII") ion source; (xxvi) a Solvent Assisted Inlet Ionisation ("SAII") ion source; (xxvii) a Desorption Electrospray Ionisation ("DESI") ion source; and (xxviii) a Laser Ablation Electrospray Ionisation ("LAESI") ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The spectrometer may comprise an electrostatic ion trap or mass analyser that employs inductive detection and time domain signal processing that converts time domain signals to mass to charge ratio domain signals or spectra. Said signal processing may include, but is not limited to, Fourier Transform, probabilistic analysis, filter diagonalisation, forward fitting or least squares fitting.

The spectrometer may comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

The spectrometer may comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The spectrometer may comprise a chromatography or other separation device upstream of an ion source. According to an embodiment the chromatography separation device comprises a liquid chromatography or gas chromatography device. According to another embodiment the separation device may comprise: (i) a Capillary Electrophoresis ("CE") separation device; (ii) a Capillary Electrochromatography ("CEC") separation device; (iii) a substantially rigid ceramic-based multilayer microfluidic substrate ("ceramic tile") separation device; or (iv) a supercritical fluid chromatography separation device.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

Analyte ions may be subjected to Electron Transfer Dissociation ("ETD") fragmentation in an Electron Transfer Dissociation fragmentation device. Analyte ions may be caused to interact with ETD reagent ions within an ion guide or fragmentation device.

According to an embodiment in order to effect Electron Transfer Dissociation either: (a) analyte ions are fragmented or are induced to dissociate and form product or fragment ions upon interacting with reagent ions; and/or (b) electrons are transferred from one or more reagent anions or negatively charged ions to one or more multiply charged analyte cations or positively charged ions whereupon at least some of the multiply charged analyte cations or positively charged ions are induced to dissociate and form product or fragment ions; and/or (c) analyte ions are fragmented or are induced to dissociate and form product or fragment ions upon interacting with neutral reagent gas molecules or atoms or a non-ionic reagent gas; and/or (d) electrons are transferred from one or more neutral, non-ionic or uncharged basic gases or vapours to one or more multiply charged analyte cations or positively charged ions whereupon at least some of the multiply charged analyte cations or positively charged ions are induced to dissociate and form product or fragment ions; and/or (e) electrons are transferred from one or more neutral, non-ionic or uncharged superbase reagent gases or vapours to one or more multiply charged analyte cations or positively charged ions whereupon at least some of the multiply charge analyte cations or positively charged ions are induced to dissociate and form product or fragment ions; and/or (f) electrons are transferred from one or more neutral, non-ionic or uncharged alkali metal gases or vapours to one or more multiply charged analyte cations or positively charged ions whereupon at least some of the multiply charged analyte cations or positively charged ions are induced to dissociate and form product or fragment ions; and/or (g) electrons are transferred from one or more neutral, non-ionic or uncharged gases, vapours or atoms to one or more multiply charged analyte cations or positively charged ions whereupon at least some of the multiply charged analyte cations or positively charged ions are induced to dissociate and form product or fragment ions, wherein the one or more neutral, non-ionic or uncharged gases, vapours or atoms are selected from the group consisting of: (i) sodium vapour or atoms; (ii) lithium vapour or atoms; (iii) potassium vapour or atoms; (iv) rubidium vapour or atoms; (v) caesium vapour or atoms; (vi) francium vapour or atoms; (vii) $C_{60}$ vapour or atoms; and (viii) magnesium vapour or atoms.

The multiply charged analyte cations or positively charged ions may comprise peptides, polypeptides, proteins or biomolecules.

According to an embodiment in order to effect Electron Transfer Dissociation: (a) the reagent anions or negatively charged ions are derived from a polyaromatic hydrocarbon or a substituted polyaromatic hydrocarbon; and/or (b) the reagent anions or negatively charged ions are derived from the group consisting of: (i) anthracene; (ii) 9,10 diphenyl-anthracene; (iii) naphthalene; (iv) fluorine; (v) phenanthrene; (vi) pyrene; (vii) fluoranthene; (viii) chrysene; (ix) triphenylene; (x) perylene; (xi) acridine; (xii) 2,2' dipyridyl; (xiii) 2,2' biquinoline; (xiv) 9-anthracenecarbonitrile; (xv) dibenzothiophene; (xvi) 1,10'-phenanthroline; (xvii) 9' anthracenecarbonitrile; and (xviii) anthraquinone; and/or (c) the reagent ions or negatively charged ions comprise azobenzene anions or azobenzene radical anions.

The process of Electron Transfer Dissociation fragmentation may comprise interacting analyte ions with reagent ions, wherein the reagent ions comprise dicyanobenzene, 4-nitrotoluene or azulene reagent ions.

According to embodiments of the present invention, a sample is loaded onto the surface of a syringe needle assembly, which is then inserted into an ionisation region of a spectrometer through a septum. The presence of the septum obviates the need for vacuum pumping the region from which the sample is introduced into the spectrometer because the septum maintains a gas seal between the spectrometer and the outside atmosphere. Sample is then directly desorbed and/or ionised from the needle surface itself or in close proximity to the needle surface.

The present invention may provide a simple and inexpensive method of introducing a low volatility sample into a mass spectrometer and then ionising it.

BRIEF DESCRIPTION OF THE DRAWINGS

Various embodiments of the present invention will now be described, by way of example only, and with reference to the accompanying drawings in which.

DETAILED DESCRIPTION OF EMBODIMENTS

In embodiments of the present invention a device similar to that used for gas chromatography (GC) and liquid chromatography (LC) solid phase micro-extraction (SPME) introduction is used to introduce analyte into a mass spectrometer.

Figure 1A:
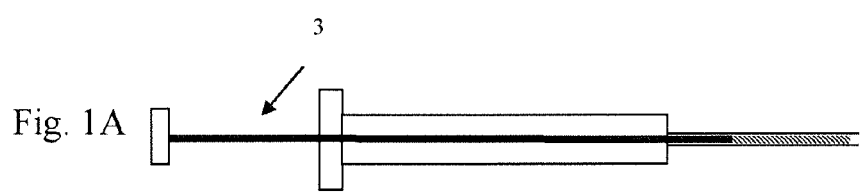
FIG. 1A shows a sample probe in the form of a syringe having a needle assembly in its retracted position.
Figure 1B:
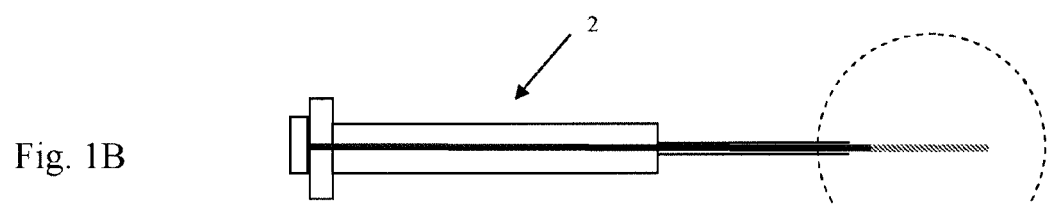
FIG. 1B shows the probe of FIG. 1A with the needle assembly in its extended position.
Figure 1C:
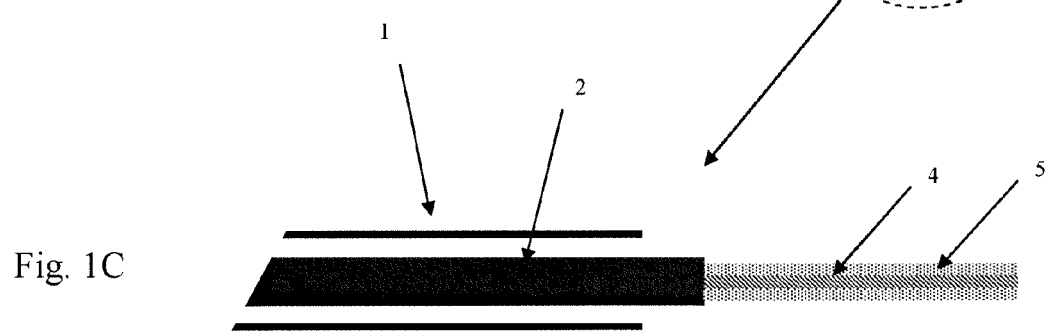
FIG. 1C show a detailed view of the end of the needle assembly shown in FIG. 1B.

FIG. 1A shows a schematic of a typical SPME syringe in its retracted position. The syringe may be used to introduce analyte through a septum and into a mass spectrometer. The septum maintains the pressure difference between the inside and outside of the mass spectrometer. FIG. 1B shows the syringe in a fully extended position. FIG. 10 shows a more detailed view of the end of the SPME device.

The syringe comprises an outer hollow needle 1 which can pierce a silica rubber septum with minimal gas leakage. The needle is attached to the syringe body 2. A stainless steel, micro-tube plunger 3 runs through the syringe body with a substantially gas tight seal so as to provide minimal air leakage through the syringe. A fused silica fibre 4 is attached to the end of the micro-tubing 3. The fibre 4 is coated with coating 5 of liquid polymer material or solid sorbent material, or a mixture of both. The coating 5 absorbs or adsorbs analytes from a sample solution, allowing efficient extraction of polar, non-polar, semi-volatile or involatile analytes from complex matrixes onto the fibre surface. Alternatively, a substrate other than the fibre may be provided for receiving the sample. The coating, fibre or other substrate may be chosen to effectively extract the chosen analyte class from a sample solution. Alternatively the analyte, with or without a matrix, may be loaded directly onto the substrate. If the fibre or substrate has a coating for absorbing or adsorbing analyte, then different coatings may be provided for different analytes. For example, polydimethylsiloxane (PDMS) coated fibre or substrate may be used to extract polar analytes. Polyacrylate-coated fibre may be used to extract highly polar analytes from polar samples. More volatile polar analytes may be extracted using a polydimethylsiloxane/divinylbenzene (PDMS/DVB) coating.

If extraction of an analyte from a sample is not required then the fibre may be uncoated. Alternatively, the fibre may be replaced with another substrate material such as, for example, a metal or glass. Analyte, with or without matrix, may then be loaded directly onto this substrate. Any residual solvent from the sample solution may be evaporated, either partially or completely, from the substrate before inserting into the mass spectrometer.

Figure 2A:
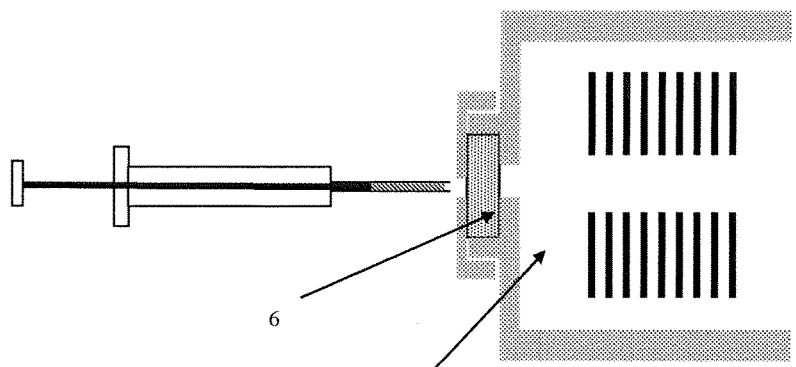
FIG. 2A shows the sample probe of FIGS. 1A-1C with the needle assembly in its retracted position and at a point just before the needle assembly is injected through a septum and into a vacuum region of a spectrometer.
Figure 2B:
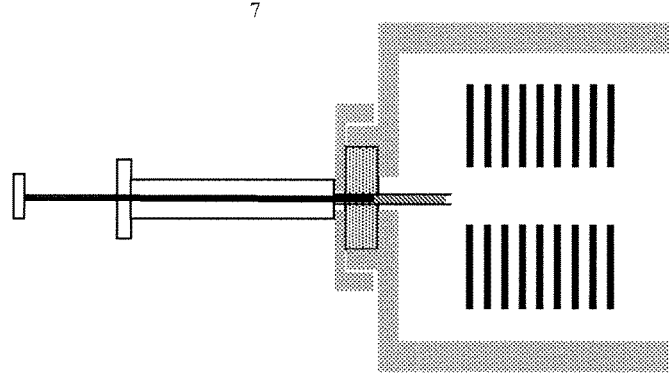
FIG. 2B shows the sample probe of FIGS. 1A-1C after the needle assembly has been injected through the septum, but whilst the needle assembly is still in its retracted position.
Figure 2C:
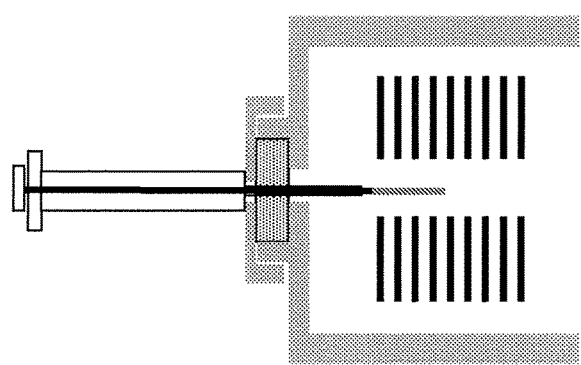
FIG. 2C shows the arrangement of FIG. 2B after the needle assembly has been moved to its extended position such that the sample is arranged within an ion guide within the vacuum chamber.

FIGS. 2A to 2C show schematics of how the analyte may be introduced into a mass spectrometer by the SPME syringe. FIG. 2A shows the syringe prior to insertion into the mass spectrometer. The fibre 4 is retracted within the hollow metal needle 1 of the syringe. The fibre has been pre-loaded with sample and is protected within the needle. The needle is then inserted through a rubber septum 6 of the mass spectrometer and into a vacuum chamber 7 of the spectrometer, as shown in FIG. 2B. The septum 6 maintains the pressure differential between the vacuum chamber and the region external to the mass spectrometer, in which the body of the syringe is located. The septum 6 makes a substantially gas tight seal with the syringe needle as it is injected through the septum so as to isolate the high pressure or atmospheric pressure external region from the vacuum chamber 7 of the mass spectrometer. The syringe plunger is then depressed so as to extend the fibre (or other substrate) on which the sample is located out from within the needle and into the vacuum chamber, as shown in FIG. 2C. The sample may then be ionised.

The vacuum chamber may comprise an RF ion guide and the fibre 4 or other substrate may enter the RF confinement region of the RF confined ion guide when the fibre or other substrate is ejected from the syringe. Any sample ionised from the surface on which the sample is located, or in proximity to the sample surface, will be efficiently trapped by the RF ion guide and transported to the analyser downstream.

The vacuum chamber 7 may be an ionisation region of the mass spectrometer and the syringe needle and/or fibre or substrate carrying the analyte is caused to protrude into the ionisation region. However, this technique may be used to introduce an analyte sample into any region of the mass spectrometer without additional vacuum pumping, since the septum maintains the pressure differential between the vacuum chamber of the mass spectrometer and the external region in which the syringe body is located. For example, the analyte sample may be introduced into any region of the mass spectrometer along the ion beam axis.

Many methods may be used for ionising the sample from the surface of the fibre or other substrate. For example, a method of ionisation may be used in which a sample is mixed with a matrix that sublimes at sub-ambient pressure, e.g. as described in MAIV-Matrix assisted ionization in vacuum. J. Am. Soc. Mass Spectrom. (2013) 24:722-732. The rapid transition of the matrix from solid to gas phase when introduced into the low pressure environment of the mass spectrometer vacuum chamber creates ions similar in nature to those created by Electrospray ionisation. Sample and matrix may be loaded onto the sample surface (i.e. the fibre or other substrate), allowed to dry and then introduced directly into an RF ion guide at sub-atmospheric pressure such as, for example, in the arrangement shown in FIG. 2. Ions formed by the MAIV process may then be transmitted into the mass spectrometer or mass analyser.

In another example, Matrix assisted laser desorption ionization (MALDI) may be used to ionise the sample directly from the surface of the fibre or other substrate. Sample and matrix may be loaded onto the fibre or other substrate and a laser may be fired directly at the fibre or other substrate surface. Using this method, the sample may easily be introduced directly into an RF confined ion guide either along the axis of the ion guide or through gaps between the electrodes of the ion guide. Ions may be formed in the ion guide by MALDI and then confined by the RF ion guide. Alternatively, ions may be formed close to the ion guide entrance and accelerated into the ion guide from the fibre or other substrate of the syringe using an electric field. Said other substrate may be electrically insulating or electrically conductive. Many MALDI substrates are known which may not require additional MALDI matrix and these may be used in the present invention. These may be applied to the syringe as coatings or may form the entirety of the substrate in the syringe.

Figure 3:
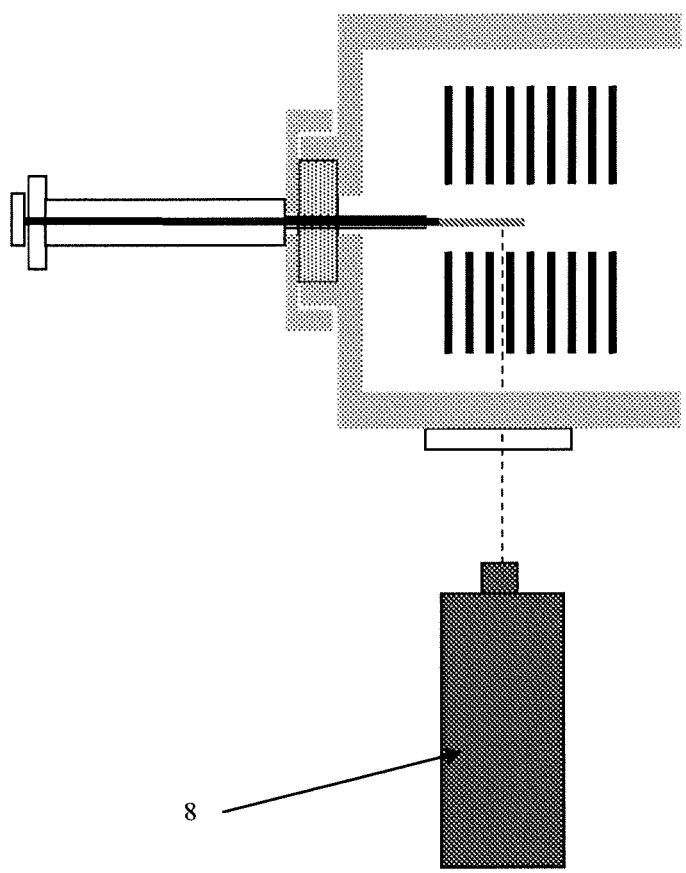
FIG. 3 shows the arrangement of FIG. 2C wherein a laser is used to ionise sample on the needle assembly.

FIG. 3 illustrates an embodiment corresponding to that of FIGS. 2A-2C, wherein analyte ions are desorbed from the syringe fibre or other substrate and then ionised by a laser or other light source 8. The path of the laser beam, shown by the dotted line, passes through the RF confining lens elements of the RF ion guide and is incident on the syringe fibre or other substrate. Ions which are created near the surface or the fibre or other substrate are confined in the RF ion guide. These ions may then be driven towards the exit of the ion guide by applying a transient DC pulse (e.g. a DC travelling wave) that moves along the axis of the ion guide, or by applying a DC voltage gradient along the ion guide.

The analyte may be ionised by ionisation techniques other than MALDI, such as glow discharge ionisation, Electron impact ionisation, Chemical ionisation, Fast Atom Bombardment (FAB), Liquid Secondary Ion Mass Spectrometry (LSIMS), metastable atom bombardment (MAB) and other ionisation techniques.

For electron impact ionisation, for example, the needle assembly may be introduced directly into the ion source volume and the sample may be desorbed by heating the needle or inner substrate.

For any of the ionisation techniques discussed herein, the needle may be heated in order to assist desorption of sample, if required. For example, the needle may be heated by resistive heating, conduction or infra-red radiation.

Alternatively, ions may be desorbed and ionised by bombardment with ions, or electrons or excited neutrals at sub-ambient pressure.

In another embodiment, sub-atmospheric pressure electrospray ionisation may be used directly from the syringe substrate itself. In this embodiment the substrate may contain or be supplied with a low flow of suitable solvent and a counter electrode provided within the needle or mass spectrometer vacuum chamber to initiate and sustain electrospray ionisation. Either the counter electrode or the needle, or both, may be set to a suitable potential to initiate the electrospray.

Figure 4:
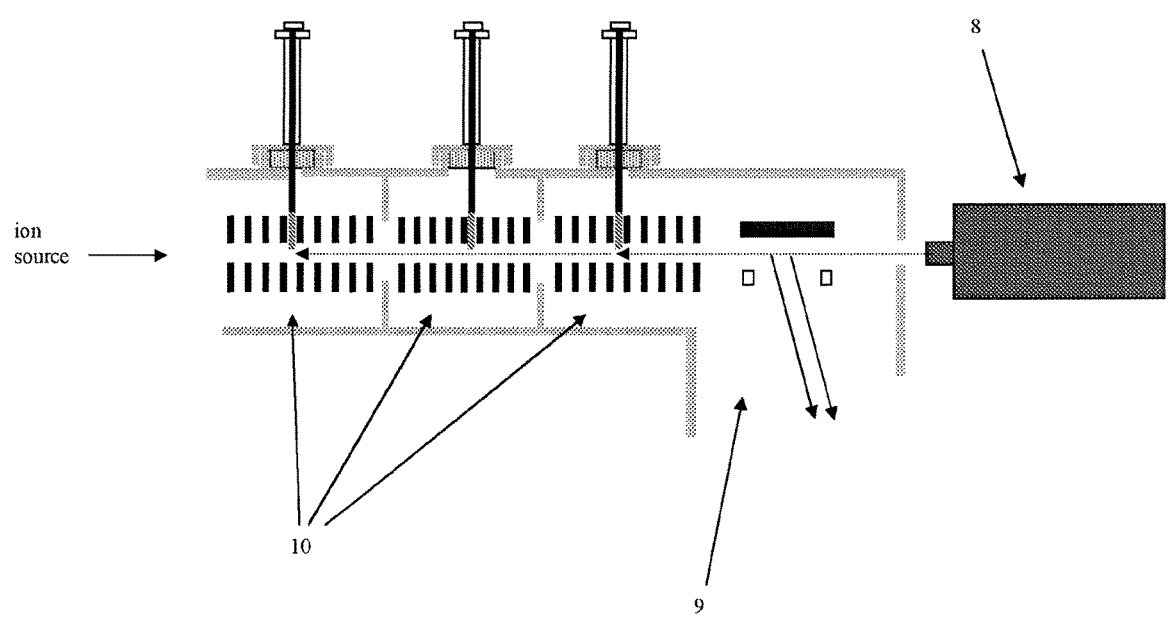
FIG. 4 shows another embodiment wherein a sample probe may be injected into various components of the spectrometer at one or more of three different locations.

FIG. 4 shows an exemplary schematic of an orthogonal time of flight mass spectrometer to illustrate the versatility of the present invention. The spectrometer comprises three RF ion guides 10, each of which is arranged in a separate vacuum chamber. The spectrometer also comprises an orthogonal time of flight mass analyser 9 downstream of the ion guides 10. A laser 8 is positioned so as to direct laser light along the ion-optical axis of the ion guides 10. One or more sample may be introduced into the spectrometer by any one of the methods described herein. The sample(s) may be introduced directly into any one of, or all of, the three RF ion guides 10 within the separate differentially pumped vacuum regions of the mass spectrometer 10. This is illustrated by the three syringes that have fibres or substrates extending into the ion guides 10. In this embodiment laser 8 illuminates the syringe fibre or substrate so as to cause the sample to be desorbed from the fibre or substrate and ionised by MALDI.

In this example sample may be introduced directly into one of the three RF confined ion guides. One or more of the RF ion guides may act as an ion trap, fragmentation cell, reaction cell, mass analyser or ion mobility analyser. Alternatively the sample may be introduced into a non-RF confined region of the mass spectrometer and electrostatic lenses may be used to accelerate and focus ions away from the surface of the syringe fibre or substrate.

Although the present invention has been described with reference to various embodiments, it will be understood by those skilled in the art that various changes in form and detail may be made without departing from the scope of the invention as set forth in the accompanying claims.

The sample introduced into the mass spectrometer by the syringe may be a reagent substance for creating reagent ions that perform ion-molecule or ion-ion interactions within a region of the mass spectrometer.

Although described as a method of introduction of low volatility samples, the present invention can be used to introduce and ionise high volatility samples or may ionise from solution. For example, sample from solution may be loaded into the needle or driven through the needle via an external delivery system. The needle may then be inserted through the septum into the vacuum region of the spectrometer.

Embodiments have been described wherein a fibre or other substrate carries the sample and wherein the fibre or other substrate is ejected from the needle of the syringe. However, alternatively, sample may be loaded onto the inner surface of the hollow needle. In this arrangement, a fibre or other substrate may not be provided and need not be ejected from the needle in use. Therefore, the sample loading device may not be a syringe, provided it comprises a needle. The sample may be desorbed from the needle, for example, by heating the needle.

The invention may be used to introduce an ionise sample in any region of the mass spectrometer and is not limited to the traditional ion source region. For example on an q-IMS-TOF, sample may be introduced and ionised after the quadrupole mass filter or after the IMS separator. Ionisation may be within an RF confined ion guide or within an RF confined mass analyser or filter, such as a 2D or 3D ion trap or quadrupole ion guide.

The needle, fibre or other substrate may have DC or RF voltage applied to it in order to assist ionisation of the sample.

Although described for a silica rubber septum, other low leak rate injection methods may be used. For example, mechanical or spring loaded injection systems available for gas chromatography applications may be used.

An on/off isolation valve may be provided on the vacuum side of the septum in order to selectively seal the orifice closed by the septum from the vacuum side. This valve allows the periodic replacement of the septum without venting the mass spectrometer.

Although less desired, an open orifice may be provided between the atmospheric and the sub-atmospheric pressure regions, wherein the orifice is substantially the same size as the outer diameter of the needle, thereby reducing the pumping requirement of the sub-atmospheric pressure region to a minimum. In this way, a septum is not required. In this case the sensitivity of the system is not limited by the orifice size as ionisation occurs within the low pressure region.

The sample injection operation described herein may be performed multiple times, providing a simple batch inlet for samples with or without pre-extraction or pre-concentration of analyte by solid phase extraction.

The introduction of the sample may be automated, for example, by using existing gas chromatography mass spectrometer (GC-MS) auto-sampler technology.

The invention claimed is:

1. A method of mass spectrometry or ion mobility spectrometry comprising:
providing a spectrometer comprising an orifice between an atmospheric pressure region and a sub-atmospheric pressure region of the spectrometer, wherein the sub-atmospheric pressure region comprises an ion guide or ion trap;
providing a sample probe comprising a needle assembly on which a sample is deposited or that is supplied with a sample;
inserting the needle assembly through the orifice and into the sub-atmospheric pressure region so that the sample is arranged within the ion guide or ion trap in the sub-atmospheric pressure region; and then
desorbing the sample from the needle assembly within the sub-atmospheric pressure region and/or ionising the sample within the sub-atmospheric pressure region so as to generate ions that enter the ion guide or ion trap;
wherein the needle assembly comprises a hollow needle and a substrate member on which the sample is located, absorbed or adsorbed; wherein the substrate member is housed within the hollow needle so as to be protected by the hollow needle, and wherein the substrate member is extendable out of the hollow needle from within the hollow needle; and
wherein said step of inserting the needle assembly through the orifice comprises inserting said hollow needle through the orifice whilst the substrate member is retracted inside the hollow needle and protected within the hollow needle; wherein when the hollow needle is inside the sub-atmospheric pressure region the substrate member is extended out from within the hollow needle; and wherein the sample on the extended substrate member is then desorbed and/or ionised.

2. The method of claim 1, wherein the spectrometer comprises a septum, film or membrane arranged over the orifice that initially forms a gas seal between the atmospheric pressure region and the sub-atmospheric pressure region, and wherein the step of inserting the needle assembly through the orifice comprises piercing the septum, film or membrane with a needle of the needle assembly whilst the substrate member is retracted inside the hollow needle and protected within the hollow needle.

3. The method of claim 1, wherein the sample deposited on the needle assembly is a sample in the solid phase.

4. The method of claim 1, wherein the needle assembly comprises a solid phase micro-extraction (SPME) device for holding the sample.

5. The method of claim 1, wherein the ion guide or ion trap is formed from electrodes and voltages are applied to said electrodes so as to confine sample ions generated from said sample in one, two or three dimensions within said ion guide or ion trap.

6. The method of claim 1, wherein the sample is ionised within the sub-atmospheric pressure region by directing a laser or other light source onto the sample; and/or by Matrix Assisted Ionization in Vacuum (MAIV); and/or by Matrix Assisted Laser Desorption Ionization (MALDI).

7. The method of claim 1, comprising heating the needle assembly.

8. The method of claim 1, comprising applying a DC and/or AC voltage to said needle assembly.

9. The method of claim 1, wherein the needle assembly forms at least a part of an electrospray ionisation ion source, and said method comprises supplying a sample solution to the needle assembly whilst the needle assembly is located in the sub-atmospheric pressure region and electrospraying the sample from the needle assembly.

10. The method of claim 1, wherein the orifice has substantially the same cross-sectional size and shape as the portion of the needle assembly that is injected through the orifice.

11. A method of mass spectrometry or ion mobility spectrometry comprising:
providing a spectrometer having an atmospheric pressure region, a sub-atmospheric pressure region comprising an ion guide or ion trap, and an orifice between the atmospheric pressure region and sub-atmospheric pressure region;
providing a sample probe comprising a needle assembly having a solid phase micro-extraction (SPME) device holding a sample in solid phase;
inserting the needle assembly through the orifice and into the sub-atmospheric pressure region so that the sample is arranged within the ion guide or ion trap in the sub-atmospheric pressure region; and then directing a laser onto the sample to ionise the sample within the sub-atmospheric pressure region so as to generate ions that enter the ion guide or ion trap;

wherein the needle assembly comprises a hollow needle and a substrate member on which the sample is located, absorbed or adsorbed; wherein the substrate member is housed within the hollow needle so as to be protected by the hollow needle, and wherein the substrate member is extendable out of the hollow needle from within the hollow needle; and wherein said step of inserting the needle assembly through the orifice comprises inserting said hollow needle through the orifice whilst the substrate member is retracted inside the hollow needle and protected within the hollow needle; wherein when the hollow needle is inside the sub-atmospheric pressure region the substrate member is extended out from within the hollow needle; and wherein the sample on the extended substrate member is then desorbed and/or ionised.

\* \* \* \* \*